(12) United States Patent
Patel

(10) Patent No.: US 11,547,661 B2
(45) Date of Patent: Jan. 10, 2023

(54) NICOLINE POUCH

(71) Applicant: Nirajkumar Karneshbhai Patel, West Melbourne, FL (US)

(72) Inventor: Nirajkumar Karneshbhai Patel, West Melbourne, FL (US)

( * ) Notice: Subject to any disclaimer, the term of this patent is extended or adjusted under 35 U.S.C. 154(b) by 0 days.

(21) Appl. No.: 17/834,006

(22) Filed: Jun. 7, 2022

(65) Prior Publication Data

US 2022/0296508 A1 Sep. 22, 2022

Related U.S. Application Data

(62) Division of application No. 17/124,717, filed on Dec. 17, 2020, now Pat. No. 11,382,861.

(51) Int. Cl.
| *A61K 9/00* | (2006.01) |
| *A61K 31/465* | (2006.01) |
| *A61K 47/02* | (2006.01) |
| *A61K 47/10* | (2017.01) |
| *A61K 47/12* | (2006.01) |
| *A61K 47/38* | (2006.01) |

(52) U.S. Cl.
CPC .......... *A61K 9/0056* (2013.01); *A61K 31/465* (2013.01); *A61K 47/02* (2013.01); *A61K 47/10* (2013.01); *A61K 47/12* (2013.01); *A61K 47/38* (2013.01)

(58) Field of Classification Search
CPC .... A61K 9/0056; A61K 31/465; A61K 47/02; A61K 47/10; A61K 47/12; A61K 47/38
See application file for complete search history.

(56) References Cited

U.S. PATENT DOCUMENTS

| 2013/0251779 A1 | 9/2013 | Svandal et al. |
| 2014/0271946 A1 | 9/2014 | Kobal et al. |
| 2020/0383373 A1 | 12/2020 | Stahl et al. |

FOREIGN PATENT DOCUMENTS

| WO | 2018197454 A1 | 11/2018 |
| WO | 2018233795 A1 | 12/2018 |

*Primary Examiner* — Robert A Wax
*Assistant Examiner* — Quanglong N Truong
(74) *Attorney, Agent, or Firm* — Epstein Drangel LLP; Robert L. Epstein

(57) ABSTRACT

The disclosure provides chewable nicotine formulations comprising an orally-acceptable nicotine salt, an orally-acceptable alcohol, flavor components, and an orally-acceptable binder in a water-permeable, water-insoluble pouch, together with methods of making and using the same.

18 Claims, No Drawings

NICOLINE POUCH

CROSS REFERENCE TO RELATED APPLICATION

This application is a divisional application of U.S. application Ser. No. 17/124,717, filed on Dec. 17, 2020, the contents of which are incorporated herein by reference.

FIELD

This disclosure relates to chewable pouch products comprising nicotine in free base and salt form, together with methods of making and using the same.

BACKGROUND

The health hazards of smoking are well-established. Products which can deliver nicotine via the oral mucosa rather than via the lungs include snuff, snus, chewing tobacco, nicotine chewing gums, and oral pouches comprising nicotine. These products face challenges in manufacturing, shelf stability, efficient nicotine delivery, and consumer acceptance. Nicotine is readily oxidized, so to enhance shelf stability, nicotine base may be stabilized in a polymer or gum matrix or provided in salt form. Nicotine free base is believed to be better absorbed through the oral mucosa than nicotine salts, so products which provide nicotine in salt form may further comprise pH-adjusting agents to raise the oral pH upon use, thereby releasing the free base. High pH products may have undesirable bitter or soapy flavors, and/or poor mouthfeel, while products where nicotine is polymer-stabilized may release nicotine relatively slowly and inefficiently. The disadvantages of these chewable products may make them unappealing to users as an alternative to smoking, even though products that deliver nicotine by smoking may present greater danger to the heart and lungs than chewable products.

There is a need for chewable nicotine delivery products, which release nicotine quickly and efficiently, have good flavor and mouthfeel, and which are stable for long-term storage.

SUMMARY

The disclosure provides a chewable nicotine product, comprising nicotine base, nicotine salt, flavor, and binder in a water-permeable, water-insoluble pouch, wherein nicotine and flavor are released when the pouch is chewed, and wherein the product provides good nicotine release, flavor, mouthfeel, and shelf-stability.

For example, in one embodiment, the disclosure provides a chewable nicotine formulation comprising nicotine, an orally-acceptable nicotine salt, an orally-acceptable alcohol, flavor components, and binder in a water-permeable, water-insoluble pouch.

In another embodiment, the disclosure provides a method for making a pouch comprising nicotine, nicotine acid addition salt, propylene glycol, flavor, and binder, wherein the nicotine acid addition salt is formulated in nonaqueous conditions, using propylene glycol as solvent, and products made thereby.

In another embodiment, the disclosure provides a method of delivering nicotine, for example a method of nicotine replacement therapy, comprising administering the above-described chewable pouch to a subject in need thereof.

Further areas of applicability of the present disclosure will become apparent from the detailed description provided hereinafter. It should be understood that the detailed description and specific examples, while indicating certain preferred embodiments of the disclosure, are intended for purposes of illustration only and are not intended to limit the scope of the disclosure.

DETAILED DESCRIPTION

The formulations of the disclosure are non-aqueous formulations, comprising nicotine and orally-acceptable acid to form a nicotine acid addition salt in an orally-acceptable alcohol solvent (e.g., propylene glycol), together with flavor and binder, in a water-permeable, water-insoluble pouch. Alcohols, such as propylene glycol, have a much lower dielectric constant than water, so the nicotine and orally-acceptable acid dissolved in the alcohol do not produce ions to the same extent as they would in water, which has unpredictable effects on salt formation, relative to salt formation in aqueous solution. It is found that the nicotine acid addition salt provided thereby is stable relative to nicotine in entirely free base form, but also provides a better mouth feel and nicotine delivery than a nicotine salt formed in aqueous solution.

In a first embodiment, the disclosure provides a chewable nicotine formulation comprising nicotine, an orally-acceptable nicotine salt, an orally-acceptable alcohol, flavor components, and an orally-acceptable binder in a water-permeable, water-insoluble pouch (Formulation 1). For example, the disclosure provides the following formulations:

1.1. Formulation 1 wherein the orally-acceptable nicotine salt is selected from nicotine hydrochloride, nicotine dihydrochloride, nicotine monotartrate, nicotine bitartrate, nicotine sulphate, nicotine zinc chloride monohydrate, nicotine pyruvate, nicotine phosphate, nicotine salicylate, nicotine malate, nicotine carbonate, nicotine bicarbonate, nicotine acetate, nicotine citrate, nicotine folate, nicotine fumarate, nicotine lactate, and nicotine benzoate.

1.2. Any foregoing formulation wherein the orally-acceptable nicotine salt is a salt of an orally-acceptable organic acid.

1.3. Any foregoing formulation wherein the orally-acceptable nicotine salt is a salt of an orally-acceptable monoprotic organic acid.

1.4. Any foregoing formulation wherein the orally-acceptable nicotine salt is nicotine benzoate.

1.5. Any foregoing formulation wherein the molar ratio between nicotine free base and orally-acceptable nicotine salt is 1:1 to 1:10.

1.6. Any foregoing formulation wherein the molar ratio between nicotine free base and nicotine acid addition salt is about 1:2.

1.7. Any foregoing formulation wherein the formulation comprises an orally-acceptable acid, e.g., selected from hydrochloric acid, tartaric acid, pyruvic acid, phosphoric acid, salicylic acid, malic acid, carbonic acid, acetic acid, citric acid, tartaric acid, folic acid, fumaric acid, lactic acid, and benzoic acids; e.g., benzoic acid.

1.8. Any foregoing formulation wherein the orally-acceptable alcohol is propylene glycol.

1.9. Any foregoing formulation wherein the binder is selected from polysaccharides, polyols, sugars, natural fibers, microcrystalline cellulose, cellulose and cellulose derivatives, and mixtures thereof.

1.10. Any foregoing formulation wherein the binder is a hydroscopic but insoluble material.

1.11. Any foregoing formulation wherein the binder comprises microcrystalline cellulose.

1.12. Any foregoing formulation wherein the water-permeable, water insoluble pouch is made of a semi-permeable material which substantially prevents the binder from leaving the bag but permits saliva and therein dissolved components from the powder in the pouch to freely pass through said material.

1.13. Any foregoing formulation wherein the water-permeable, water insoluble pouch is made from one or more polymers or fibers safe for oral use, e.g., selected from polypropylene, low density polyethylene, polyethylene terephthalate, polyurethane, polyvinyl acetate, polyvinyl alcohol, polystyrene, poly(ethylene-vinyl acetate), rayon, silk, cotton, polyester, cellulosic materials (e.g., hydroxypropyl cellulose), and combinations thereof.

1.14. Any foregoing formulation further comprising one or more additional components selected from antioxidants, emulsifiers, preservatives, and solvents.

1.15. Any foregoing formulation further comprising a neutral, orally-acceptable mineral salt, e.g., selected from sodium chloride, potassium chloride, and mixtures thereof, e.g., comprising potassium chloride.

1.16. Any foregoing formulation which is substantially free of any basic ingredient other than nicotine.

1.17. Any foregoing formulation which is substantially free of water.

1.18. Any foregoing formulation which is made under substantially water-free conditions.

1.19. Any foregoing formulation, wherein the contents of the water-permeable, water-insoluble pouch have a pH of less than 7, e.g., pH 5.5 to pH 6.9, e.g., about pH 6.5, when measured in a 10% slurry in water.

1.20. Any foregoing formulation, wherein the ratio by weight of (i) binder and (if present) neutral orally-acceptable mineral salt, e.g., potassium chloride, to (ii) nicotine, orally-acceptable nicotine salt, orally-acceptable alcohol, and flavor, is from 70:30 from 50:50, e.g., 65:35 to 55:45, e.g. about 60:40.

1.21. Any foregoing formulation wherein the orally-acceptable nicotine salt is nicotine benzoate, the orally-acceptable alcohol is propylene glycol, and the orally-acceptable binder is microcrystalline cellulose.

1.22. Any foregoing formulation wherein the contents of the water-permeable, water-insoluble pouch consist of nicotine, nicotine benzoate, potassium chloride, propylene glycol, flavor, and binder.

1.23. Any foregoing formulation wherein the contents of the water-permeable, water-insoluble pouch consist of nicotine, nicotine benzoate, potassium chloride, propylene glycol, flavor, and microcrystalline cellulose.

1.24. Any foregoing formulation wherein the flavor components are pH neutral.

1.25. Any foregoing formulation wherein the flavor components comprises one or more flavors selected from mint oil, menthol, watermelon, blueberry, pomegranate, strawberry, blueberry, dragonfruit, and cucumber flavors.

1.26. Any foregoing formulation wherein the flavor components comprise mint oil and/or menthol.

1.27. Any foregoing formulation wherein the nicotine comprises synthetic nicotine. 1.28. Any foregoing formulation wherein the nicotine comprises nicotine from tobacco. 1.29. Any foregoing formulation wherein the nicotine has an (R):(S) isomeric ratio of greater than 1.

1.30. Any foregoing formulation wherein the contents of the water-permeable, water-insoluble pouch are in dry powder form.

1.31. Any foregoing formulation comprising 1%-9%, e.g. 2-5%, e.g., 2.5-3.5%, of nicotine and orally-acceptable nicotine salts, by weight of the contents of the water-permeable, water-insoluble pouch.

1.32. Any foregoing formulation comprising 4-20%, e.g., 5%-15%, e.g., about 5%, or about 10%, or about 15%, of orally-acceptable alcohol, e.g. propylene glycol, by weight of the contents of the water-permeable, water-insoluble pouch.

1.33. Any foregoing formulation comprising 50%-70%, e.g. 55%-60%, of binder, e.g., microcrystalline cellulose, by weight of the contents of the water-permeable, water-insoluble pouch.

1.34. Any foregoing formulation comprising 0.5%-2%, e.g., 1%-1.5%, of orally-acceptable mineral salt, e.g. potassium chloride, by weight of the contents of the water-permeable, water-insoluble pouch.

1.35. Any foregoing formulation wherein the contents of the water-permeable, water-insoluble pouch comprise:
Nicotine: 1% to 6%, e.g. 1% to 3%, e.g., 2%
Benzoic acid: 0.5% to 3%, e.g., 0.5% to 1.5%, e.g., 1%
Propylene glycol: 5% to 20%
Flavor: 20% to 35%
Microcrystalline cellulose: 55% to 60%
Potassium chloride: 1% to 1.5%
wherein all amounts are by weight of the contents of the pouch,
wherein the nicotine and benzoic acid may be in free or salt form or mixtures thereof, and
wherein the weight of the nicotine is calculated as the free base equivalent and the weight of the benzoic acid is calculated as the free acid equivalent, irrespective of the actual proportions of nicotine and benzoic acid in free or salt form.

1.36. Formulation 1.35 wherein the weight percent of the solid components comprising microcrystalline cellulose and potassium chloride is 55% to 65%, e.g., about 60%; and the weight percent of the liquid components comprising propylene glycol, nicotine, benzoic acid and flavor is 35% to 45%, e.g., about 40%.

1.37. Formulation 1.35 or 1.36 wherein the weight ratio of nicotine to benzoic acid is 1:1 to 3:1, e.g., about 2:1.

1.38. Formulation 1.35, 1.36 or 1.37 wherein the molar ratio of nicotine to benzoic acid is 3:1 to 1:3, e.g., from 2:1 to 1:1, e.g., is about 3:2.

1.39. Any foregoing formulation wherein each pouch contains a dose of 1 mg to 15 mg nicotine, e.g., 5-10 mg nicotine, e.g., about 8 mg nicotine, wherein the weight of the nicotine is calculated as the free base equivalent, irrespective of whether the nicotine is in free base or salt form.

1.40. Any foregoing formulation wherein the weight of the contents of the pouch is from 0.2 g to 1 g, e.g. from 0.3 g to 0.5 g, e.g., about 0.4 g.

1.41. Any foregoing formulation when made according to any of Methods 1, et seq.

1.42. Any foregoing formulation for use in a method of delivering nicotine to a subject, e.g. a person in need of nicotine replacement therapy.

1.43. Any foregoing formulation wherein the formulation has a shelf life of at least 6 months, e.g. at temperatures up to 40° C.

1.44. Any foregoing formulation wherein the formulation has a pH of less than 7, e.g., pH 5.5 to pH 6.9, e.g., about pH 6.5, when measured in a 10% slurry in water, and exhibits improved stability, mouth feel, and/or flavor relative to a product having a pH of at least 8 when measured in a 10% slurry in water.

In another embodiment, the disclosure provides a method (Method 1) of making a chewable nicotine formulation, e.g., according to any of Formulation 1 above, comprising the steps of
- a) dissolving nicotine and an orally-acceptable acid in a non-aqueous orally-acceptable solvent,
- b) adding flavor components,
- c) mixing with solid orally-acceptable binder and optionally a salt, and
- d) filling a water-permeable, water-insoluble pouch with the mixture thus obtained.

For example, Method 1 comprises 1.1. Method 1 wherein the orally-acceptable acid is selected from hydrochloric acid, tartaric acid, pyruvic acid, phosphoric acid, salicylic acid, malic acid, carbonic acid, acetic acid, citric acid, tartaric acid, folic acid, fumaric acid, lactic acid, and benzoic acids.

1.2. Any foregoing method wherein the orally-acceptable acid is an organic acid.

1.3. Any foregoing method wherein the orally-acceptable acid is a monoprotic organic acid.

1.4. Any foregoing method wherein the orally-acceptable acid is benzoic acid.

1.5. Any foregoing method wherein the molar ratio between nicotine and orally-acceptable acid in step a) is from 3:1 to 1:3, e.g., from 2:1 to 1:1.

1.6. Any foregoing method wherein the molar ratio between nicotine and orally-acceptable acid in step a) is about 3:2.

1.7. Any foregoing method wherein the orally acceptable acid is benzoic acid, and the weight ratio of weight ratio of nicotine to benzoic acid in step a) is 1:1 to 3:1, e.g., about 2:1.

1.8. Any foregoing method wherein the nonaqueous solvent comprises propylene glycol, e.g. wherein the nonaqueous solvent is propylene glycol.

1.9. Any foregoing method wherein the nonaqueous solvent is heated to facilitate dissolution of the nicotine and the orally-acceptable acid.

1.10. Any foregoing method wherein the binder is selected from polysaccharides, polyols, sugars, natural fibers, microcrystalline cellulose, cellulose and cellulose derivatives, and mixtures thereof.

1.11. Any foregoing method wherein the binder is a hydroscopic but insoluble material.

1.12. Any foregoing method wherein the binder comprises microcrystalline cellulose.

1.13. Any foregoing method wherein the water-permeable, water insoluble pouch is made of a semi-permeable material which substantially prevents the binder from leaving the bag but permits saliva and therein dissolved components from the powder in the pouch to freely pass through said material.

1.14. Any foregoing method wherein the water-permeable, water insoluble pouch is made from one or more polymers or fibers safe for oral use, e.g., selected from polypropylene, low density polyethylene, polyethylene terephthalate, polyurethane, polyvinyl acetate, polyvinyl alcohol, polystyrene, poly(ethylene-vinyl acetate), rayon, silk, cotton, polyester, cellulosic materials (e.g., hydroxypropyl cellulose), and combinations thereof.

1.15. Any foregoing method further comprising adding one or more additional components selected from antioxidants, emulsifiers, preservatives, and solvents.

1.16. Any foregoing method further comprising adding to the binder a neutral alkali salt, e.g., selected from sodium chloride, potassium chloride, and mixtures thereof, e.g., potassium chloride.

1.17. Any foregoing method wherein no basic ingredient is added other than nicotine.

1.18. Any foregoing method wherein all steps are carried out under substantially water-free conditions.

1.19. Any foregoing method wherein the product of step b) has an apparent pH of 5 to less than 7, e.g. about 5.5-6.5, when measured using a pH-sensitive glass electrode concentrically surrounded by a reference electrode filled with reference electrolyte, which measures the $H^+$ ion concentration of the solution.

1.20. Any foregoing method, wherein the product of step c) has a pH of less than 7, e.g., pH 5.5 to pH 6.9, e.g., about pH 6.5, in a 10% slurry in water.

1.21. Any foregoing method, wherein the ratio by weight of (i) binder and (if present) neutral alkali salt, e.g., potassium chloride, to (ii) nicotine, nicotine benzoate, propylene glycol, and flavor in the product of step c) is from 70:30 from 50:50, e.g., 65:35 to 55:45, e.g. about 60:40.

1.22. Any foregoing method wherein the product of step c) consists of nicotine, nicotine benzoate, potassium chloride, propylene glycol, flavor, and binder.

1.23. Any foregoing method wherein the product of step c) consists of nicotine, nicotine benzoate, potassium chloride, propylene glycol, flavor, and microcrystalline cellulose.

1.24. Any foregoing method wherein the flavor components are pH neutral.

1.25. Any foregoing method wherein the flavor components comprise one or more flavors selected from mint oil, menthol, watermelon, blueberry, pomegranate, strawberry, blueberry, dragonfruit, and cucumber flavors.

1.26. Any foregoing method wherein the flavor components comprise mint oil and/or menthol.

1.27. Any foregoing method wherein the nicotine comprises synthetic nicotine. 1.28. Any foregoing method wherein the nicotine comprises nicotine from tobacco.

1.29. Any foregoing method wherein the nicotine has an (R):(S) isomeric ratio of greater than 1.

1.30. Any foregoing method wherein the product of step c) in dry powder form.

1.31. Any foregoing method wherein the product of step c) comprises 2-5%, e.g., 2.5-3.5%, of nicotine and nicotine salts, by weight.

1.32. Any foregoing method wherein the product of step c) comprises 4-20%, e.g., 5%-15%, e.g., about 5%, or about 10%, or about 15%, of propylene glycol, by weight.

1.33. Any foregoing method wherein the product of step c) comprises 50%-70%, e.g. 55%-60%, of microcrystalline cellulose, by weight.

1.34. Any foregoing method wherein the product of step c) comprises 0.5%-2%, e.g., 1%-1.5%, of potassium chloride, by weight.

1.35. Any foregoing method wherein:
- in step a), the amount of nicotine is 1% to 3%, e.g., 2%, the orally-acceptable acid is benzoic acid in an amount of 0.5% to 1.5%, e.g., 1%, and the non-aqueous orally-acceptable solvent is propylene glycol, in an amount of 5% to 20%;
- in step b), the amount of flavor components is 20% to 35%; and
- in step c), the solid binder is microcrystalline cellulose in the amount of 55% to 60% and a salt is present which is potassium chloride in the amount of 1% to 1.5%;

wherein all amounts are given by weight of the product of step c).

1.36. The foregoing method wherein the weight percent of the microcrystalline cellulose plus the potassium fluoride is 55% to 65% and the weight percent of the propylene glycol plus the flavor is 35% to 40%.

1.37. Any foregoing method wherein in step d), each pouch is filled with a mixture of the product of step c) containing 1 mg to 10 mg nicotine (weight given as free base equivalent).

1.38. Any foregoing method, wherein the product is any of Formula 1, et seq.

In a further embodiment, the disclosure provides a method of delivering nicotine to a subject comprising administering a chewable nicotine formulation according to any of Formulation 1, et. seq. to the subject, e.g., a needed, e.g., up to 3× daily, e.g., wherein the subject is a patient in need of nicotine replacement therapy.

Example 1: Nicotine Pouch Formulations

Formulation A—

The following components are combined as described above:

| Name of Material | Absolute Quantity(% w/w) |
|---|---|
| Nicotine | 2.00% |
| Benzoic acid | 2.00% |
| Propylene glycol | 14.40% |
| Flavor Mix | 21.60% |
| MCC | 58.84% |
| Potassium Chloride | 1.16% |
| Total | 100% |

The propylene glycol is heated in a heated mixing tank to 70° C. Benzoic acid is added and mixed until it completely dissolves. Then nicotine is added and mixed well. Flavor components are added one by one and mixed to form a liquid premix. Microcrystalline cellulose (MCC) and potassium chloride are mixed in a ribbon blender, then the liquid premix mixture is added to the microcrystalline cellulose (MCC) and potassium chloride in the ribbon blender and all ingredients are mixed well, to form a powder. The powder is then measured to provide the desired dose of nicotine and placed in pouches.

Formulation B—

The following components are combined as described above:

| Name of Material | Absolute Quantity(% w/w) |
|---|---|
| Nicotine | 2.00% |
| Benzoic acid | 2.00% |
| Propylene glycol | 4.00% |
| Flavor Mix | 32.00% |
| MCC | 58.84% |
| Potassium Chloride | 1.16% |
| Total | 100% |

Formulation C—

The following components are combined:

| Name of Material | Absolute Quantity(% w/w) |
|---|---|
| Nicotine | 2.00% |
| Benzoic acid | 1.00% |
| Propylene glycol | 5.00% |
| Flavor Mix | 32.00% |
| MCC | 58.84% |
| Potassium Chloride | 1.16% |
| Total | 100% |

Formulation D—

The following components are combined as described above:

| Name of Material | Absolute Quantity(% w/w) |
|---|---|
| Nicotine | 2.00% |
| Benzoic acid | 1.00% |
| Propylene glycol | 15.40% |
| Flavor Mix | 21.60% |
| MCC | 58.84% |
| Potassium Chloride | 1.16% |
| Total | 100% |

Formulation E—

The following components are combined as described above:

| Name of Material | Absolute Quantity(% w/w) |
|---|---|
| Nicotine | 2.00% |
| Benzoic acid | 1.00% |
| Propylene glycol | 15.40% |
| Flavor Mix | 21.60% |
| MCC | 60% |
| Total | 100% |

Formulation F—

The following components are combined as described above:

| Name of Material | Absolute Quantity(% w/w) |
|---|---|
| Nicotine | 2.00% |
| Benzoic acid | 1.00% |
| Propylene glycol | 5.00% |
| Flavor Mix | 32.00% |
| MCC | 60% |
| Total | 100% |

Example 2: Nicotine Pouch Formulation Performance

The liquid premixes for Formulations C, D, E and F have an apparent pH of about 6.5, while the liquid premixes for Formulations A and B have an apparent pH of about 5.5, when measured using a standard pH sensor (i.e., a pH-sensitive glass electrode concentrically surrounded by a reference electrode filled with reference electrolyte, which measures the $H^+$ ion concentration of a solution). Note that while this measurement is not a true pH, as the liquid premixes are non-aqueous, it provides a useful measure of comparative proton activity.

Formulations A and B, having higher levels of benzoic acid, are tested and found to have inferior mouth feel relative to Formulations C and D. Formulations C and D provide a "tingling" sensation, which is preferred by users.

Formulations C and D, which have potassium chloride, are found to provide a fresher, cleaner taste compared to Formulations E and F, which do not contain potassium chloride.

Various solvents are tested, including other alcohols. Propylene glycol is preferred over other solvents, as it is found to dissolve both the acid and the nicotine efficiently and without excessive heating, which is important, as heating can cause the nicotine to volatilize and can generate toxic fumes.

The invention claimed is:

1. A method of making a nicotine pouch formulation comprising nicotine free base, an orally-acceptable nicotine salt, propylene glycol, flavor components, and an orally-acceptable binder in a water-permeable, water-insoluble pouch, wherein the nicotine pouch formulation is substantially free of tobacco material, comprising the steps of
   a) dissolving nicotine free base and an orally-acceptable acid in the propylene glycol,
   b) adding the flavor components,
   c) mixing with the orally-acceptable binder and optionally a salt, and
   d) filling the water-permeable, water-insoluble pouch with the mixture thus obtained.

2. A method of delivering nicotine to a subject comprising administering to the subject a nicotine pouch formulation comprising nicotine free base, an orally-acceptable nicotine salt, propylene glycol, flavor components, and an orally-acceptable binder in a water-permeable, water-insoluble pouch, wherein the nicotine pouch formulation is substantially free of tobacco material, wherein the orally-acceptable nicotine salt is prepared by dissolving nicotine free base and an orally-acceptable acid in the propylene glycol, and further wherein the subject is a patient in need of nicotine replacement therapy.

3. The method of claim 2, wherein the orally-acceptable nicotine salt is nicotine benzoate.

4. The method of claim 2, wherein the molar ratio between nicotine free base and orally-acceptable nicotine salt is about 1:2.

5. The method of claim 2, wherein the binder comprises microcrystalline cellulose.

6. The method of claim 2, wherein the formulation further comprising a neutral, orally-acceptable mineral salt.

7. The method of claim 2, wherein the formulation is substantially free of any basic ingredient other than nicotine.

8. The method of claim 2, wherein the formulation is made under substantially water-free conditions.

9. The method of claim 2, wherein the contents of the water-permeable, water-insoluble pouch have a pH of less than 7, when measured in a 10% slurry in water.

10. The method of claim 2, wherein the ratio by weight of
    (i) binder and (if present) neutral orally-acceptable mineral salt, to
    (ii) nicotine, orally-acceptable nicotine salt, propylene glycol, and flavor, is from 70:30 to 50:50.

11. The method of claim 2, wherein the orally-acceptable nicotine salt is nicotine benzoate and the orally-acceptable binder is microcrystalline cellulose.

12. The method of claim 2, wherein the contents of the water-permeable, water-insoluble pouch are in dry powder form.

13. The method of claim 2, wherein the formulation comprises
1%-9% of nicotine and orally-acceptable nicotine salts;
4% to 20% of propylene glycol;
50%-70% of binder;
0.5%-2% of orally-acceptable mineral salt,
wherein all percentages are by weight of the contents of the water-permeable, water-insoluble pouch.

14. The method of claim 2, wherein the contents of the water-permeable, water-insoluble pouch comprise:
    a) Nicotine: 1% to 6%
    b) Benzoic acid: 0.5% to 3%
    c) Propylene glycol: 5% to 20%
    d) Flavor: 20% to 35%
    e) Microcrystalline cellulose: 55% to 60%
    f) Potassium chloride: 1% to 1.5%
wherein all amounts are by weight of the contents of the water-permeable, water-insoluble pouch,
wherein the nicotine and benzoic acid are in free or salt form or mixtures thereof, and
wherein the weight of the nicotine is calculated as the free base equivalent and the weight of the benzoic acid is calculated as the free acid equivalent, irrespective of the actual proportions of nicotine and benzoic acid in free or salt form.

15. The method of claim 14, wherein the weight percent of the solid components comprising microcrystalline cellulose and potassium chloride is 55% to 65%; and the weight percent of the liquid components comprising propylene glycol, nicotine, benzoic acid and flavor is 35% to 45%.

16. The method of claim 14, wherein the weight ratio of nicotine to benzoic acid is 1:1 to 3:1.

17. The method of claim 2, wherein each pouch contains a dose of 1 mg to 15 mg nicotine, wherein the weight of the nicotine is calculated as the free base equivalent, irrespective of whether the nicotine is in free base or salt form.

18. A liquid comprising nicotine free base, benzoic acid, nicotine benzoate, propylene glycol, and flavor components, wherein the liquid is substantially free of water.

\* \* \* \* \*